United States Patent [19]
Peterson

[11] Patent Number: 5,649,912
[45] Date of Patent: Jul. 22, 1997

[54] AMPULE FILLING DEVICE

[75] Inventor: Steven F. Peterson, West Linn, Oreg.

[73] Assignee: Bioject, Inc., Portland, Oreg.

[21] Appl. No.: 603,563

[22] Filed: Feb. 21, 1996

Related U.S. Application Data

[63] Continuation of Ser. No. 207,290, Mar. 7, 1994, abandoned.

[51] Int. Cl.$^6$ ............................................. A61M 5/00
[52] U.S. Cl. ........................ 604/187; 604/232; 604/200
[58] Field of Search .......................... 604/68–72, 140, 604/141, 143, 228, 232, 233, 187, 88–99, 240, 414, 200, 201, 210; 128/760; 206/537

[56] References Cited

U.S. PATENT DOCUMENTS

| | | |
|---|---|---|
| 2,221,739 | 11/1940 | Reiter . |
| 2,545,017 | 3/1951 | Billingsley . |
| 2,547,099 | 4/1951 | Smoot . |
| 2,605,763 | 8/1952 | Smoot . |
| 2,635,601 | 4/1953 | May . |
| 2,653,605 | 9/1953 | Hein, Jr. . |
| 2,667,874 | 2/1954 | Dickinson, Jr. . |
| 2,688,965 | 9/1954 | Huber . |
| 2,704,543 | 3/1955 | Scherer ............................ 604/68 |
| 2,720,880 | 10/1955 | Whitaker et al. . |
| 2,764,977 | 10/1956 | Ferguson . |
| 2,828,743 | 4/1958 | Ashkenaz et al. . |
| 2,859,750 | 11/1958 | Stroop . |
| 2,922,419 | 1/1960 | Bednarz . |
| 2,986,141 | 5/1961 | Hart . |
| 3,110,309 | 11/1963 | Higgins . |
| 3,115,133 | 12/1963 | Morando . |
| 3,853,125 | 12/1974 | Clark et al. ............................ 604/70 |
| 4,055,177 | 10/1977 | Cohen ............................ 604/88 |
| 4,338,980 | 7/1982 | Schwebel et al. ............................ 141/18 |
| 4,515,586 | 5/1985 | Mendenhall et al. ............................ 604/87 |
| 4,662,878 | 5/1987 | Lindmayer ............................ 604/401 |
| 4,936,841 | 6/1990 | Aoki et al. ............................ 604/413 |
| 5,064,413 | 11/1991 | McKinnon et al. . |
| 5,281,198 | 1/1994 | Haber et al. ............................ 604/86 |
| 5,364,386 | 11/1994 | Fukuoka et al. ............................ 604/411 |
| 5,468,232 | 11/1995 | Naganuma ............................ 604/200 |

FOREIGN PATENT DOCUMENTS

| | | |
|---|---|---|
| 93/00842 | 1/1992 | WIPO . |
| 92/00951 | 7/1992 | WIPO . |

*Primary Examiner*—Michael Powell Buiz
*Assistant Examiner*—V. Alexander
*Attorney, Agent, or Firm*—Lyon & Lyon LLP

[57] ABSTRACT

An ampule filling device having an ampule for jet injection attached to a transfer apparatus having a housing, a barrier within the housing, and a push rod attached to the housing to drive the medication from a medication vial. Further, the ampule filling device is advantageously bulk sterilized during assembly, and, assembled and packaged in an aseptic manufacturing environment.

23 Claims, 9 Drawing Sheets

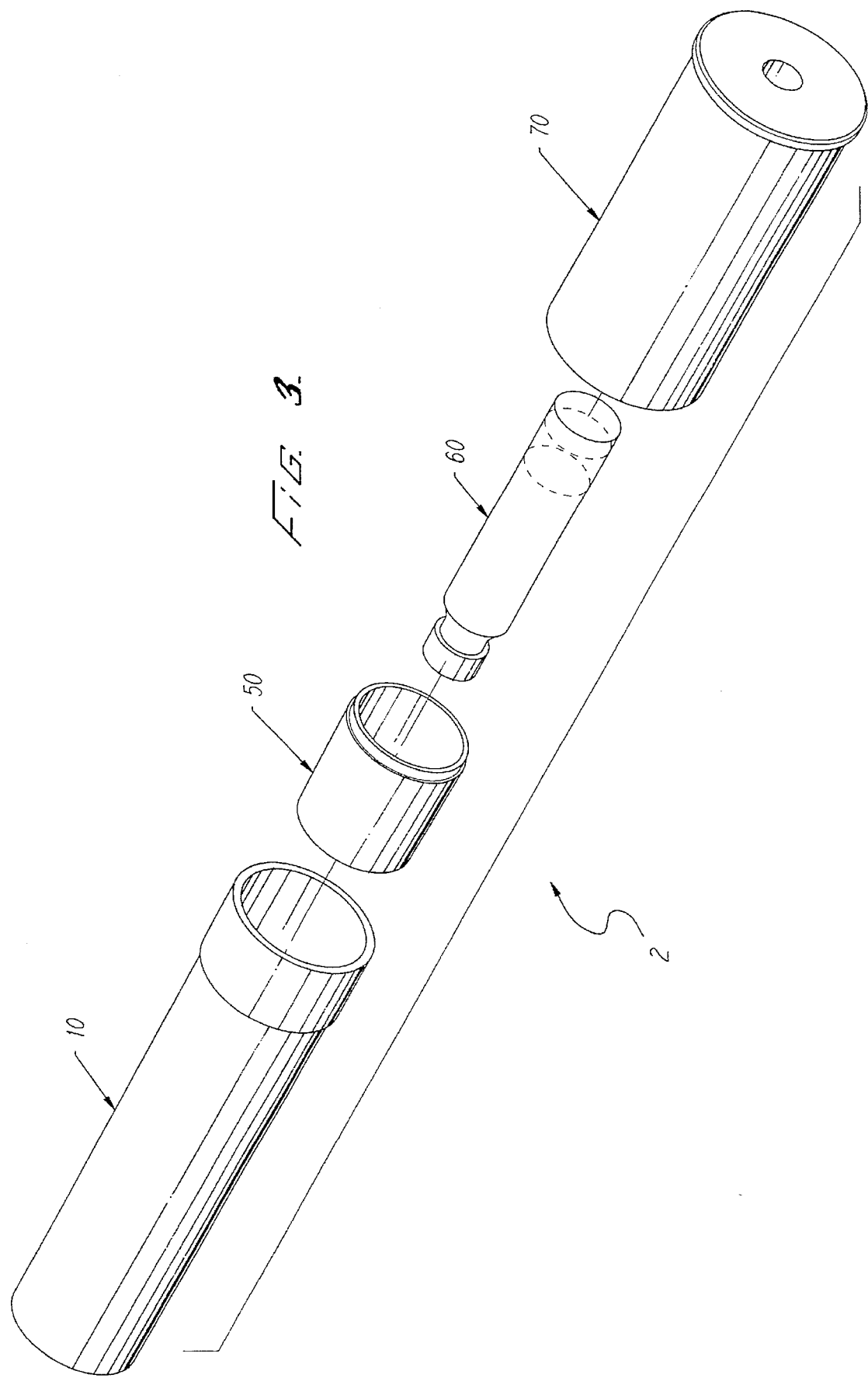

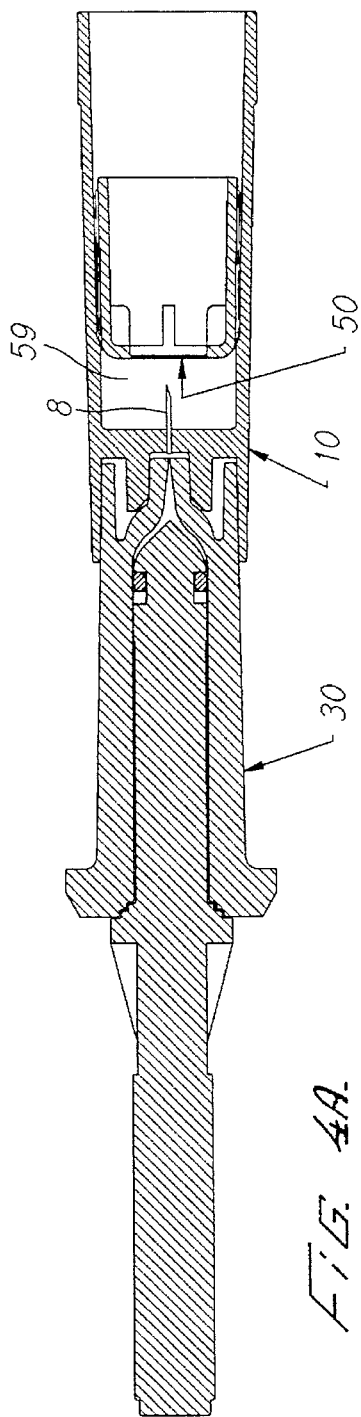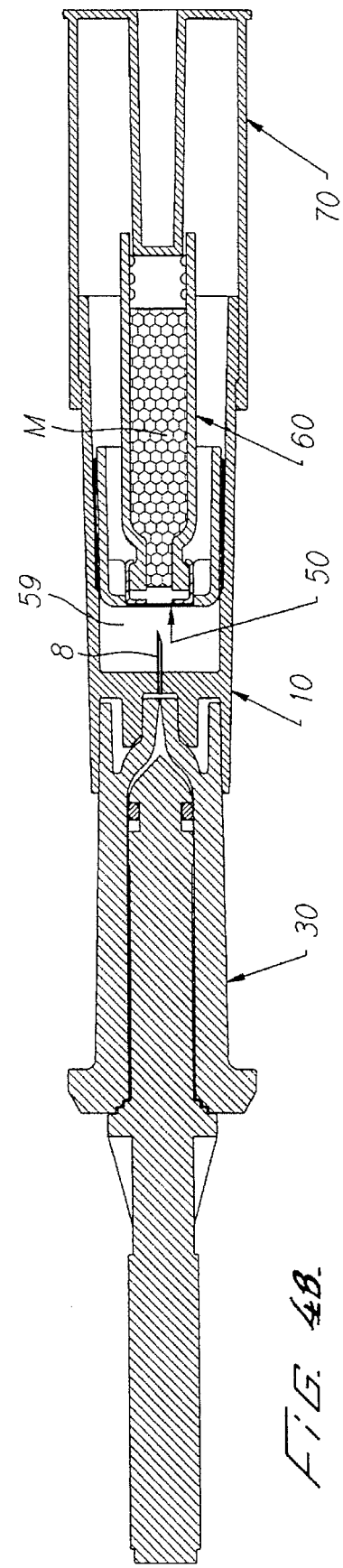

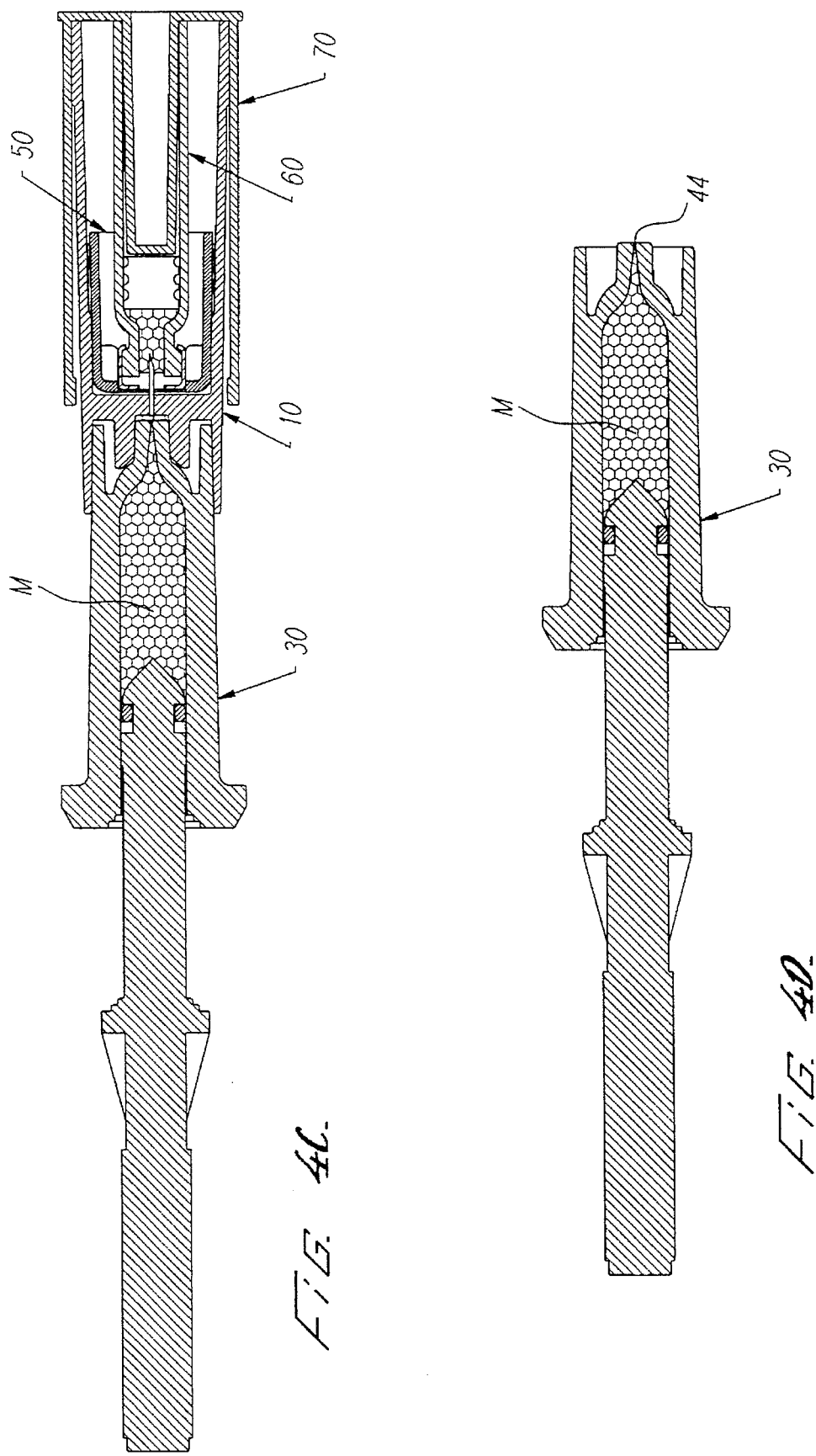

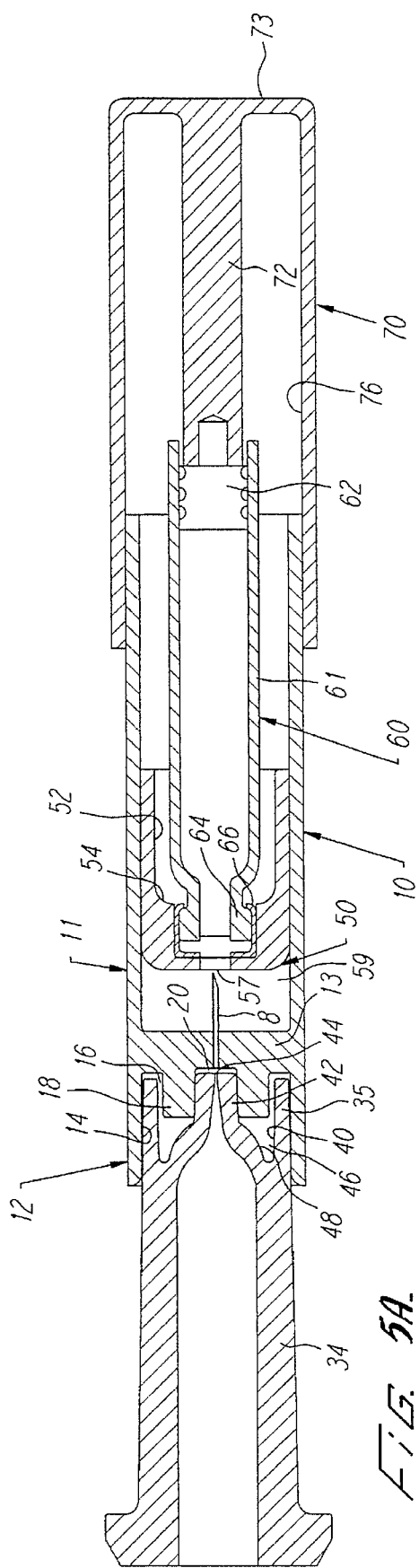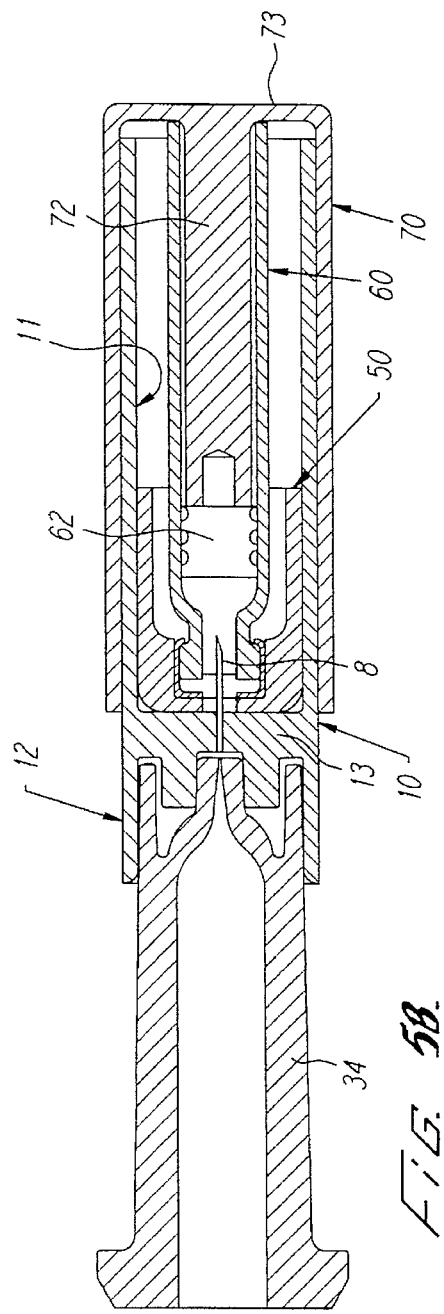
FIG. 5A.
FIG. 5B.

AMPULE FILLING DEVICE

This is a continuation of application Ser. No. 08/207,290, filed on Mar. 7, 1994, now abandoned, and which designated the U.S.

FIELD OF THE INVENTION

This invention relates to needle-free hypodermic jet injection, specifically to an ampule filling device for ampules used in needle-free hypodermic jet injection.

BACKGROUND OF THE INVENTION

Needle-free hypodermic jet injection has been known in the past. In jet injection devices, either springs, electric drivers, or pressurized gas is often used to drive a plunger. The plunger, in turn, advances within an ampule causing liquid medication to be ejected with sufficient velocity to penetrate the skin of a patient. Prior to operation, the ampules must be filled with medication. Usually a filling needle attached to the ampule is used to draw medication from a standard medication vial into the ampule. Thus, it has long been recognized that a pre-filled ampule for jet injection is advantageous due to its ease of use, convenience, and improved control over medication administration. However, sale of a pre-filled ampule would require costly and time consuming regulatory approval.

Most medications for injection are currently packaged in glass containers with rubber or elastomeric closures on one or both ends. The glass, primarily, lacks the strength required to withstand the stresses of jet injection, thus making the glass medication vials unsuitable for use in jet injection. Furthermore, adequate mechanical support for the common glass medication vial, to prevent its breakage during jet injection, has yet to be developed. In addition to the strength problem of the glass, the elastomeric closures or plugs are not designed to withstand the pressure levels required for jet injection. Moreover, it would be relatively expensive and time consuming to modify, for jet injection, the medication vials that are currently in use. Modification would require extensive development, testing, and regulatory approvals.

Therefore, it would be desirable to have a device that efficiently and conveniently transfers medication from the glass medication vials, that are currently in use, to the ampules used in jet injection, and, to have a device that improves control over medication administration, maintains a sterile medication environment, is easy to use, and is relatively inexpensive and easy to produce.

SUMMARY OF THE INVENTION

The ampule filling device of the present invention comprises an ampule for jet injection attached to a transfer apparatus. The transfer apparatus further comprises a housing adapted to attach to the ampule, a barrier within the housing to guide and support a filled medication vial, and a push rod attached to the housing to drive the medication from a medication vial.

Preferably, the components of the ampule filling device are constructed separately of molded plastic. In addition, the ampule filling device is advantageously bulk sterilized during assembly, and, assembled and packaged in an aseptic manufacturing environment.

An object of this invention is to provide an improved ampule filling device.

Further objects and advantages of the present invention will become apparent from a consideration of the drawings and ensuing description.

BRIEF DESCRIPTION OF THE DRAWINGS

FIG. 3 is an exploded perspective view of the transfer apparatus.

FIG. 4A is a longitudinal cross-sectional view of the ampule, housing, and barrier subassembly.

FIG. 4B is a longitudinal cross-sectional view of a medication vial and a push rod fitted to the subassembly depicted in FIG. 4A. The ampule filling device is depicted in its fully assembled pre-use unengaged configuration.

FIG. 4C is a longitudinal cross-sectional view depicting the fully assembled ampule filling device in FIG. 4*b* in its engaged configuration. The medication has been transferred from the medication vial into the disposable ampule.

FIG. 4D is a longitudinal cross-sectional view of a filled ampule. The ampule is separated from the transfer apparatus and ready for installation into a jet injection device.

FIG. 5A is partially an enlarged longitudinal cross-sectional view of the assembly depicted in FIG. 4B. The ampule's plunger is not depicted.

FIG. 5B is partially an enlarged longitudinal cross-sectional view of the assembly depicted in FIG. 4C. The ampule's plunger is not depicted.

DESCRIPTION OF THE PREFERRED EMBODIMENT

Figure 1:
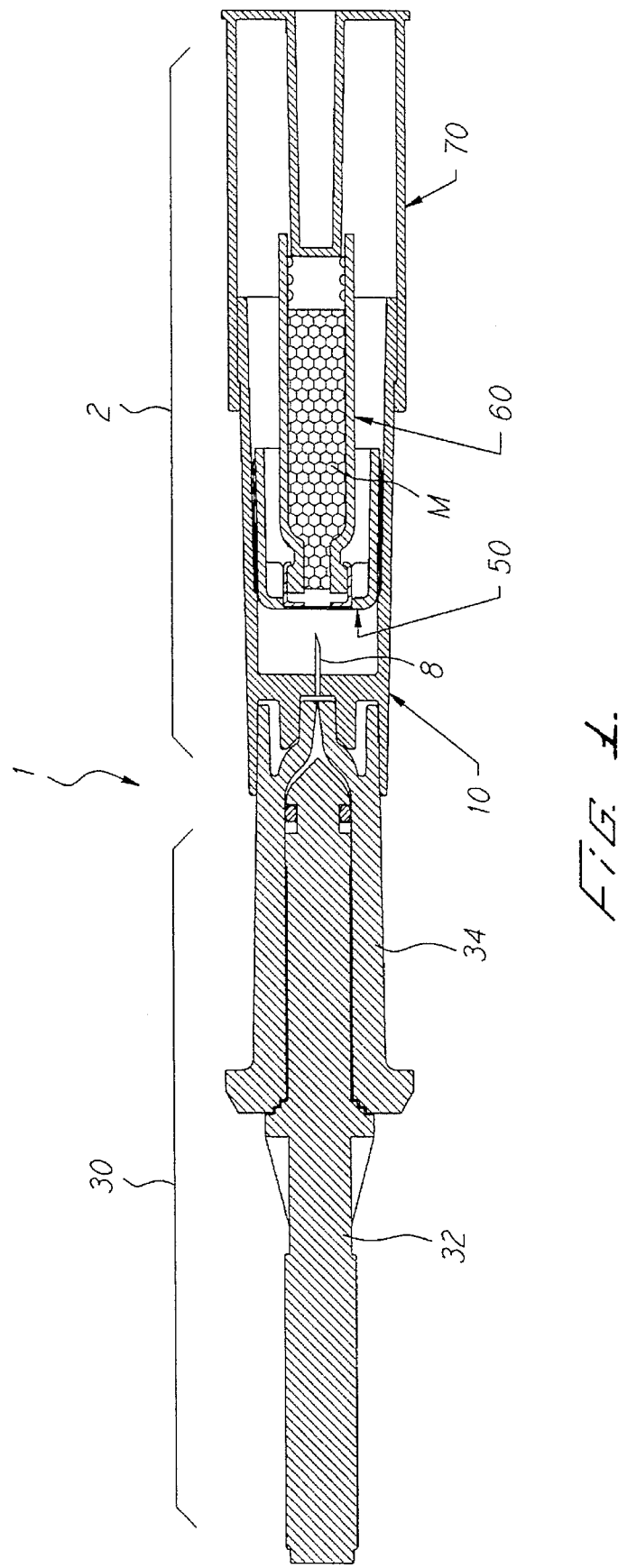
FIG. 1 is a longitudinal cross-sectional view of an assembled ampule filling device.

Referring now in detail to the drawings, therein illustrated is a novel ampule filling device 1, which as shown in FIG. 1 in a longitudinal cross-sectional view, is fully assembled and comprises a disposable unfilled ampule 30 for jet injection and a transfer apparatus 2. The major components comprising the ampule 30 are an ampule body 34 and a corresponding plunger 32. The main components of the transfer apparatus 2 comprise a housing 10, a piercing cannula 8, a barrier 50, and a push rod 70. In a preferred construction, the ampule 30, the housing 10, the piercing cannula 8, the barrier 50, and the push rod 70 are preferably formed separately of molded plastic. Located within the assembled transfer apparatus 2 is a glass medication vial 60.

Figure 2:
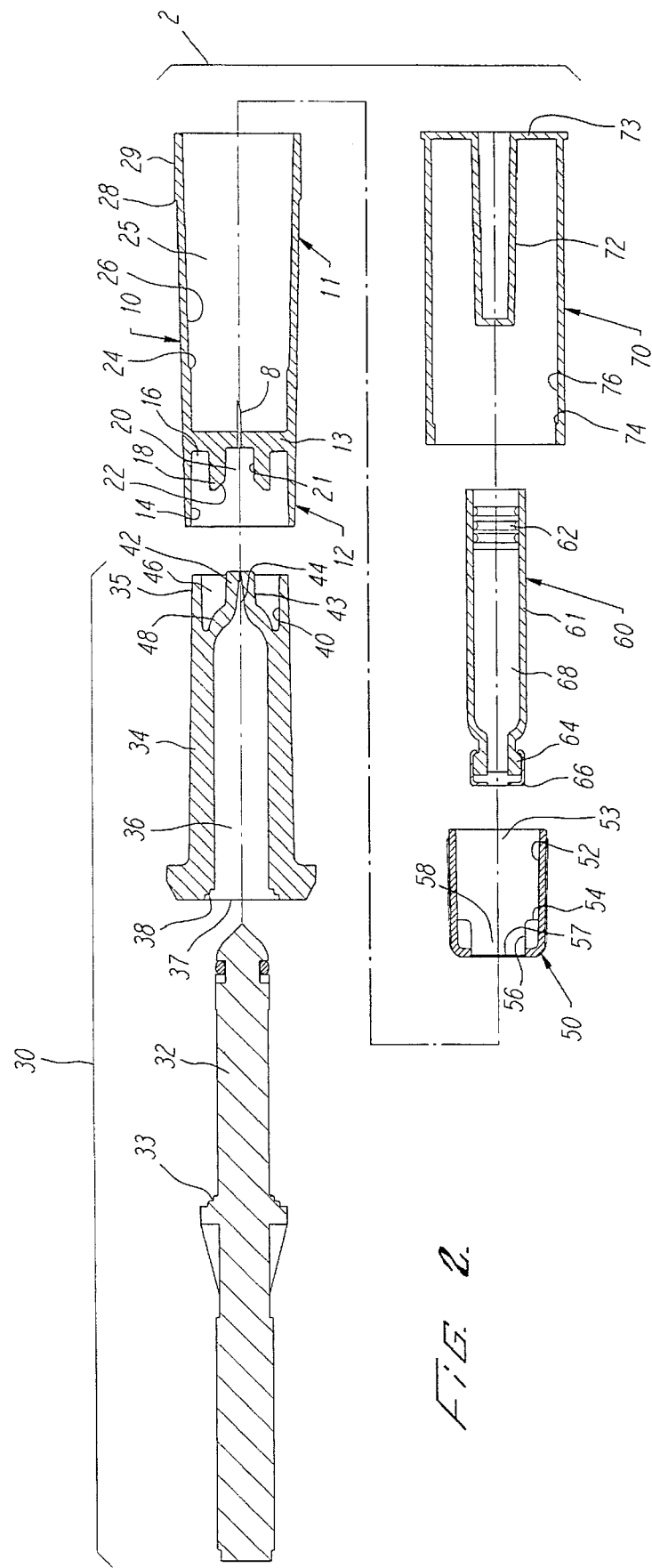
FIG. 2 is an longitudinal exploded cross-sectional view of the ampule filling device.

Turning now to FIG. 2, this is a longitudinal exploded cross-sectional view of the ampule filling device 1, which depicts the structural details of the components of the ampule 30 and transfer apparatus 2 more clearly.

The housing 10 of the transfer apparatus 2, as depicted in FIG. 3, is generally cylindrically shaped. Referring to FIG. 2, the housing 10 preferably includes a supply chamber 11 and a transfer chamber 12 separated by a partition 13. The supply chamber 11 has a cylindrical cavity defined by an inner wall 26 of the housing 10, with the partition 13 forming the well of the cavity. The inner wall 26 has a shoulder 24. The outer wall 29 of the housing 10 has a similar shoulder 28.

The transfer chamber 12 is defined by the housing 10 and a cylindrical stem 18 recessed inwardly from the end of the housing 10. The stem 18 extends axially outwardly from the partition 13 and has an axially located cylindrical cavity 20. The cavity 20 is formed by an inner stem wall 21 with the partition 13 forming the well of the cavity 20. The inner stem wall 21 is tapered inwardly as the wall 21 extends towards the partition 13, thus forming a female half of a Luer slip taper fitting. An inner edge bevel 22 is on the cavity's 20 open end. An inner wall 14 of the housing 10 forms a toroidal cavity 16 with the stem 18, wherein the partition 13 forms the well of the cavity 16.

A tubular piercing cannula 8 is located within the housing 10, and is axially fixed in the partition 13. The piercing cannula's 8 location begins at the transfer chamber 12 side of the partition 13, wherein the cannula's 8 blunt end opens into the cavity 20 of the stem 18, then extends through the partition 13 axially and inwardly into the cavity 25 of the supply chamber 11, wherein the cannula 8 forms a piercing end.

The barrier 50, as depicted in FIG. 3, is generally cylindrically cup shaped. Referring back to FIG. 2, the barrier 50 has an inner wall 52 forming a cylindrical cavity 53 in which the wall 52 steps down at a step 54 to an inner wall 56 to form a smaller cylindrical vial receiver cavity 58. A thin barrier wall 57 forms the well of the cavity 58.

The medication vial 60, located within the transfer apparatus 2, is also shown to be cylindrically shaped in FIG. 3. Referring back to FIG. 2, the medication vial 60 is comprised of a glass vial housing 61 which forms a cylindrical vial cavity 68 used to store medication M (detailed in FIG. 1). Axially located within the vial cavity 68 is a piston 62. The piston 62 slides longitudinally within the vial cavity 68. The vial housing 61 includes a vial head 64. The vial head 64 is covered by an elastomeric closure 66 to cover an opening in the head 64.

A push rod 70 is cylindrically shaped as depicted in FIG. 3. The push rod 70 is configured, referring to FIG. 2, such that a rod 72 extends axially inwardly from the push rod end 73. In addition, a shoulder catch 74 is configured on the push rod's 70 inner wall 76.

An ampule 30 comprises a generally cylindrically shaped ampule body 34 and a plunger 32. The ampule body 34 extends, on one end of the ampule body 34, co-axially around a nozzle 42 to form a tubular shroud 35, wherein the nozzle 42 generally extends beyond the tubular shroud 35. The inner wall 40 of the tubular shroud 35 and the outer nozzle wall 43 form a toroidal cavity 46; wherein a surface 48 between the inner wall 40 and the nozzle wall 43, shown generally as concave-convex but may be generally bevelled, forms the well of the cavity 46. The outer nozzle wall 43 is tapered inwardly, as it extends outwardly from the ampule body 34, such that it forms the male half of a Luer slip tapered fitting.

Further, the ampule body 34 forms a cylindrical medication storage cavity 36. Access to the storage cavity 36 is through an orifice 44 in the nozzle 42 on one end of the ampule body 34, and an opening 37 wherein the plunger 32 enters the cavity 36 on the other end of the ampule body 34. The opening 37 has a step 38 on its inner edge. The plunger 32, which axially locates and longitudinally slides within the cavity 36, has a corresponding step 33 configured on its exterior.

Preferably, the ampule filling device is first partially assembled using the untitled ampule 30, the housing 10, and the barrier 50 (see FIG. 4A). The barrier 50 is axially and slidably located within the housing 10. Then the nozzle 42 end of the ampule 30 is axially joined to the transfer chamber 12 of the housing 10. To accomplish this union the tubular shroud of the nozzle 42 end of the ampule 30 communicates with the toroidal cavity 16 of the transfer chamber 12. The inwardly sloped inner wall 14 of the housing 10 assists in holding the ampule 30 in place. Additionally, the nozzle 42 is slip-fitted into the cylindrical cavity 20 of the stem 18 with sufficient force such that the tapered outer nozzle wall 43 and tapered inner cavity wall 21 form a leak-proof connection of the Luer slip type tapered fitting. Further, the beveled inner edge 22 of the stem 18 communicates with the well surface 48 as the stem 18 extends into the toroidal cavity 46 of the nozzle 42 end of the ampule 30. This connection also acts to axially locate the ampule 30 within the transfer chamber 12 end of the housing 10.

Upon completion of this assembly, this subassembly is then advantageously bulk sterilized to sterilize the fluid pathway between the supply chamber 11 and transfer chamber 12, which includes the cavity 25 in front of the barrier 50 and continues through the piercing cannula 8 and the orifice 44 in the nozzle 42. Next, the subassembly is axially fitted with the medication vial 60 and the push rod 70 in an aseptic manufacturing assembly environment. (see FIGS. 4B and 5A).

The medication vial 60 is axially located within the housing 10 by fitting the vial head 64, and accompanying elastomeric closure 66, into the vial receiver cavity 58 of the barrier 50. The push rod 70 is then axially attached to the housing 10, wherein the inner wall 76 of the push rod 70 is slidably located on the outer wall 29 of the housing. Next, the assembled ampule filling device is packaged in final protective packaging for shipment to an end user.

Prior to use, and during shipment to the end user, the barrier 50 and medication vial 60 maintain a predetermined spacing 59 from the piercing cannula 8 within the housing 10. (discussed in detail with regards to FIG. 6).

In operation, to use the ampule filling device 1, the end user simply presses the push rod 70 on the push rod end 73 causing the push rod 70 to longitudinally slide along the outer wall 29 of the housing 10. The rod 72 longitudinally axially drives the medication vial 60 and the barrier 50 through the pre-determined spacing 59, into the piercing cannula 8. This driving action causes the piercing cannula 8 to penetrate the thin barrier wall 57 and the elastomeric closure 66, and continue on into the medication vial 60. Further motion on the push rod 70 drives the medication vial piston 62 longitudinally forward, driving the medication M out of the vial cavity 64 of the medication vial 60, through the piercing cannula 8 and on through the orifice 44 of the nozzle 42 into the medication storage cavity 36 of the ampule 30. (see FIGS. 4C and 5B) The filled ampule 30 is then separated from the transfer apparatus 12, ready for installation into a jet injection device. (see FIG. 4D)

Figure 6:
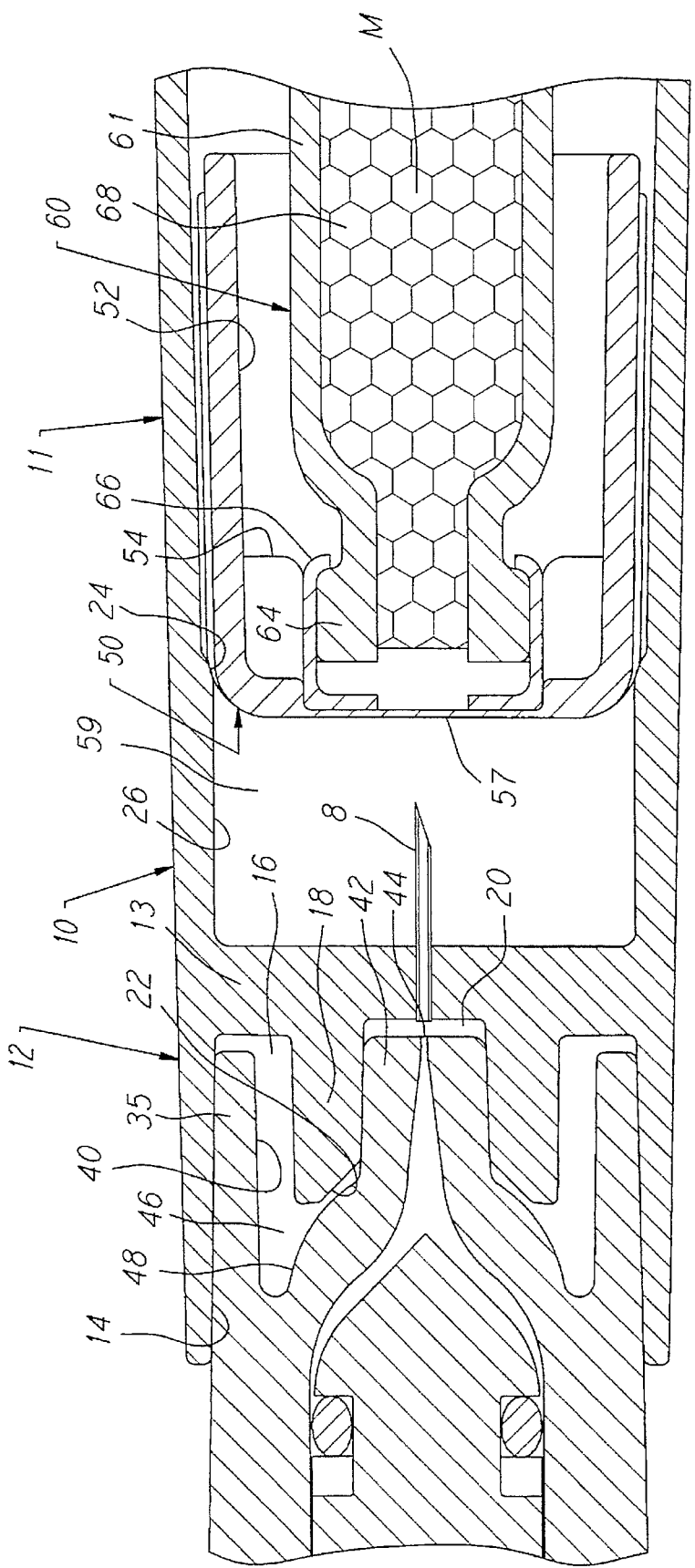
FIG. 6 is an enlarged longitudinal cross-sectional fragmented view of the ampule, housing, piercing cannula, barrier, and medication vial assembly as depicted in FIG. 4B and FIG. 5A.

Turning to FIG. 6, the pre-determined spacing 59 between the barrier 50 and the piercing cannula 8 is shown. The barrier 50 rests on the shoulder 24, located on the inner wall 26 of the housing 10, to keep the barrier 50, and the medication vial 60, separated from the piercing cannula 8 until the point of use. The shoulder 24 is sized to allow the barrier 50 to overcome the shoulder 24 when the push rod 70 is pressed, and to retain the barrier 50 during normal handling and shipping.

Figure 7:
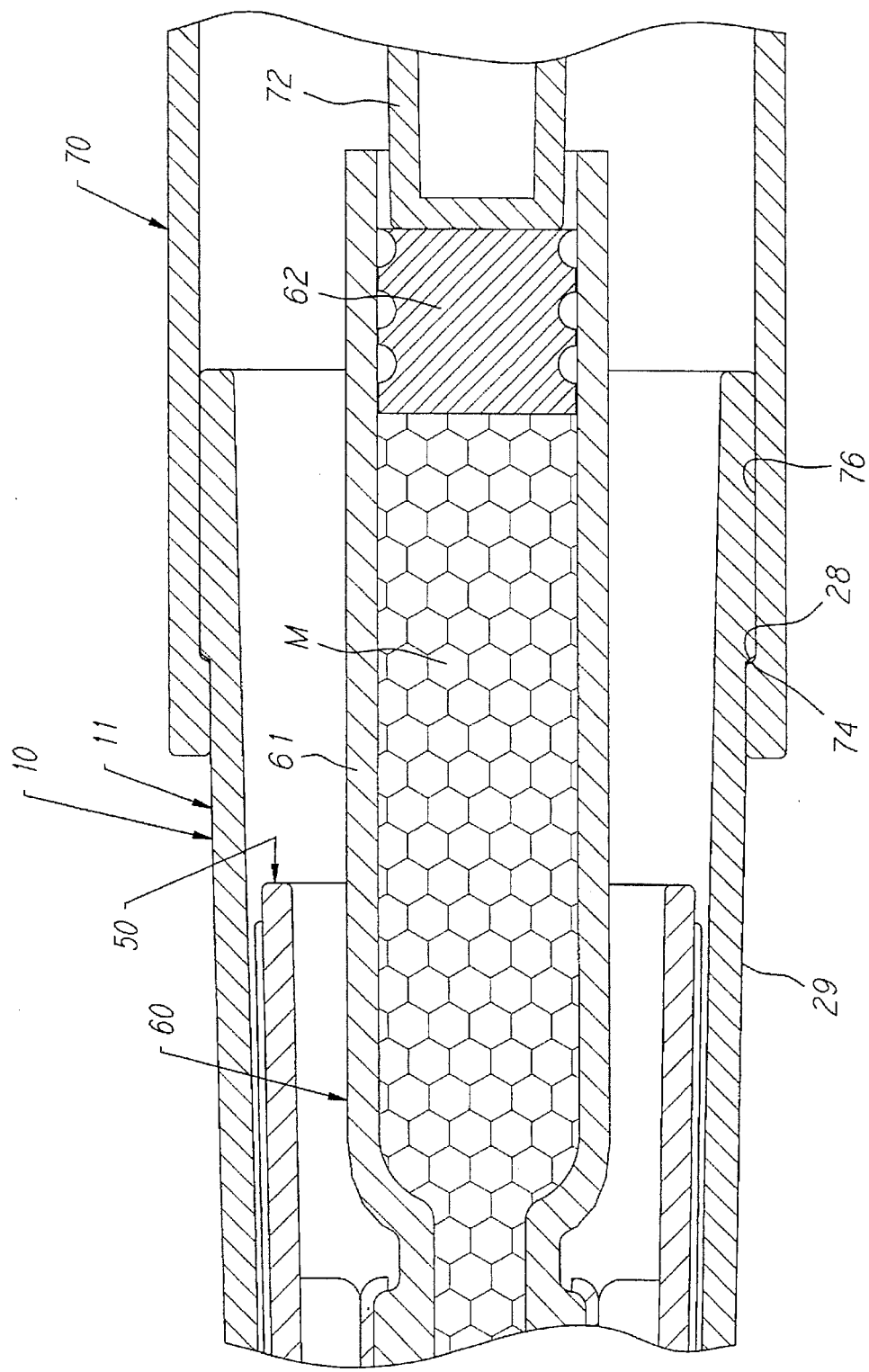
FIG. 7 is an enlarged longitudinal cross-sectional fragmented view of the housing, barrier, medication vial, and push rod assembly as depicted in FIG. 4B and FIG. 5A.

Further turning to FIG. 7, the pre-use configuration of the push rod 70, housing 10, barrier 50, and medication vial 60 is shown. The push rod 70 is retained on the housing 10, during normal handling and shipping, by a shoulder 28 on the housing's 10 outer wall 29 and the shoulder catch 74 on the push rod's 70 inner wall 76.

Figure 8:
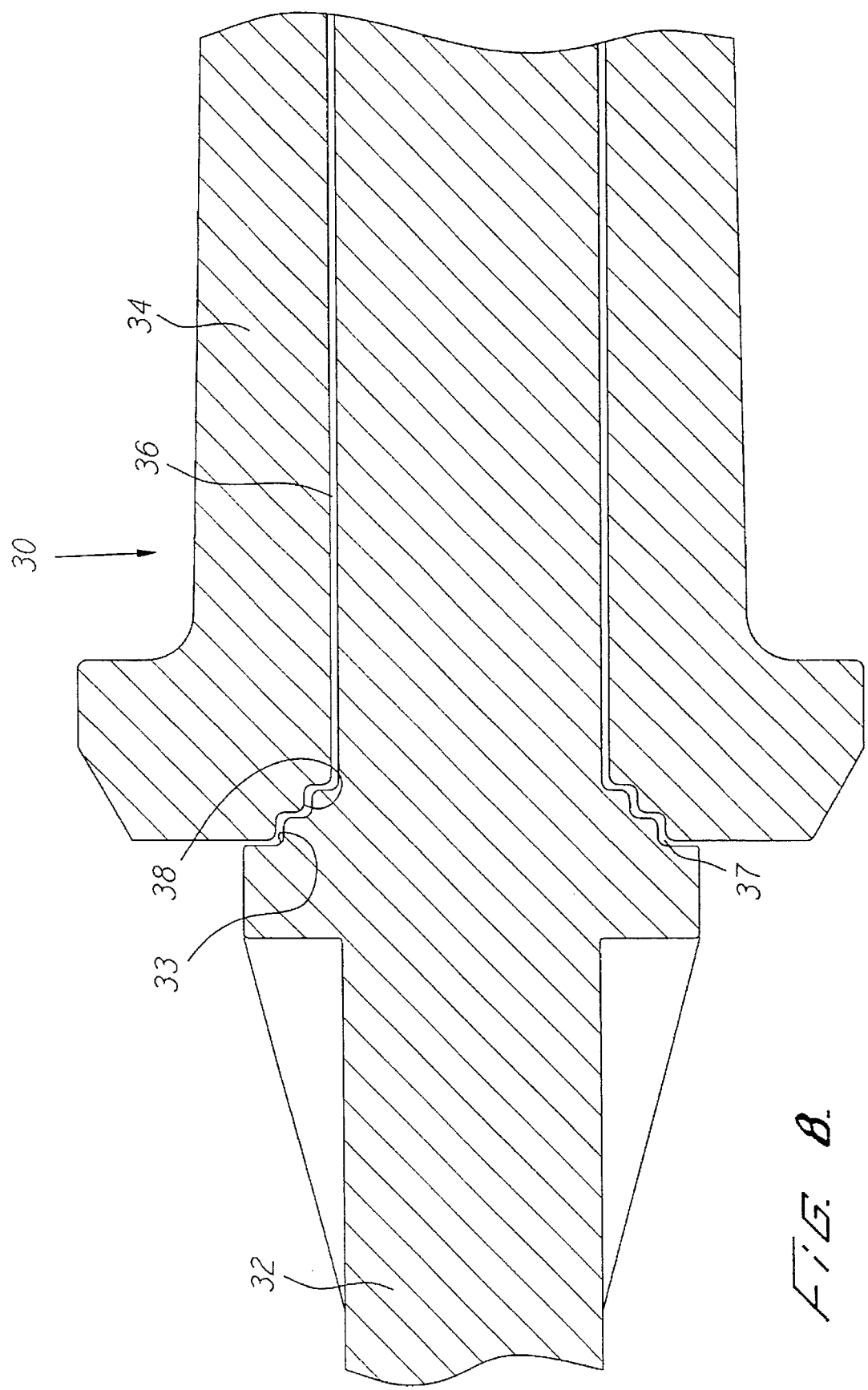
FIG. 8 is an enlarged longitudinal cross-sectional view of the plunger and ampule body. The plunger and ampule body are in the pre-filled configuration.

Referring now to FIG. 8, the pre-use configuration of the ampule 30 is shown, showing the ampule body 34 and the ampule plunger 32 assembly. The storage cavity step 38 and the corresponding plunger step 33 form a tortuous path sterility barrier. The tortuous path provides a passageway for sterilization gases to reach the storage cavity 36 of the ampule body 34, along with the fluid pathway described above, during the bulk sterilization discussed above, while also providing a pathway that, along with the barrier 50 (see also FIGS. 4A and 7), restricts the movement of microorganisms from the outside. This tortuous path configuration, along with the barrier 50 and housing 10 configuration, facilitates proper sterilization of the fluid pathway of the ampule filling device of the present invention.

While the above description contains many specificities, these should not be construed as limitations on the scope of the invention, but rather as an exemplification of one preferred embodiment thereof. Many other variations are possible.

Accordingly, the scope of the present invention should be determined not by the embodiments illustrated above, but by the appended claims and their legal equivalents.

What is claimed is:

1. An ampule filling device comprising
an ampule,
a housing releasably attached to said ampule,
a piercing cannula fixedly and axially located within said housing,
a barrier axially and slidably located within said housing adjacent an inner wall of said housing,
a medication vial having an elastomer closure and a piston axially and slidably located within said vial, said medication vial being axially received in said housing adjacent said barrier, and
a push rod axially and slidably attached to said housing, said push rod including a rod axially extending into said housing and abutting said piston in said medication vial to drive medication from said medication vial during operation of the ampule filling device.

2. The ampule filling device of claim 1, wherein said housing further comprises
a transfer chamber,
a supply chamber, and
a partition interposing and separating said transfer and supply chambers, said cannula being mounted in said partition and interconnecting said transfer and supply chambers.

3. The ampule filling device of claim 2, wherein said transfer chamber further comprises a stem extending into said transfer chamber from said partition and forming a toroidal cavity with said housing and said partition.

4. The ampule filling device of claim 3, wherein said stem includes a cavity comprising an inner wall inwardly tapered towards said partition and forming a female half of a slip taper fitting.

5. The ampule filling device of claim 1, wherein said ampule, housing, barrier, and push rod are constructed of molded plastic.

6. The ampule filling device of claim 1, wherein said barrier is generally cup shaped.

7. The ampule filling device of claim 1, wherein said housing further comprises a first shoulder formed on an inner wall of said housing, said barrier abutting said first shoulder to retain said barrier in spaced relation to said cannula prior to operation, and
a second shoulder formed on said housing to retain said push rod on said housing.

8. An ampule filling device comprising
an ampule,
a housing releasably attached to said ampule,
a piercing cannula fixedly and axially located within said housing,
a barrier axially and slidably located within said housing adjacent an inner wall of said housing, said barrier being maintained in spaced relation with said cannula prior to operation of the ampule filling device,
a medication vial having a rubber stopper axially fixed in an end of said medication vial and a piston axially and slidably located within said vial, said medication vial being axially received and retained in said barrier in said housing, and
a push rod axially and slidably attached to said housing, said push rod including a rod axially extending into said housing and abutting said piston in said medication vial to drive medication from said medication vial during operation of the ampule filling device.

9. The ampule filling device of claim 8, wherein said housing further comprises
a transfer chamber,
a supply chamber, and
a partition interposing and separating said transfer and supply chambers, said cannula being mounted in said partition and interconnecting said transfer and supply chambers.

10. The ampule filling device of claim 9, wherein said transfer chamber further comprises a stem extending into said transfer chamber from said partition and forming a toroidal cavity with said housing and said partition.

11. The ampule filling device of claim 10, wherein said stem includes a cavity comprising an inner wall inwardly tapered towards said partition and forming a female half of a slip taper fitting.

12. The ampule filling device of claim 8, wherein said housing further comprises
a first shoulder formed on said housing to retain said barrier in spaced relation to said canula prior to operation, and
a second shoulder formed on said housing to retain said push rod on said housing.

13. An ampule filling device comprising
a housing having a first and second chamber separated by a partition,
a piercing cannula axially fixed in said partition, said cannula having a first end adjacent to said first chamber and a second end extending into said second chamber,
an ampule releasably attached to said housing adjacent said first chamber,
a barrier axially and slidably located within said second chamber adjacent an inner wall of said housing, said barrier being maintained in spaced relation with said second end of said cannula prior to operation of the ampule filling device,
a medication vial having a rubber closure on one end and a piston axially and slidably located within said vial, said medication vial being received and retained by said barrier, and a push rod axially and slidably attached to said housing, said push rod including a rod axially extending into said second chamber and abutting said piston in said medication vial to drive medication from said medication vial during operation of the ampule filling device.

14. The ampule filling device of claim 13, wherein said housing further comprises
    a first shoulder formed on said housing to retain said barrier in spaced relation to said canula prior to operation, and
    a second shoulder formed on said housing to retain said push rod on said housing.

15. An ampule filling device comprising
    an ampule, said ampule comprising
        a body having first and second ends, said first end opens into a storage cavity formed in said body and said second end is formed into a nozzle,
        a plunger axially and slidably extending from said first end into said storage cavity of said body, each of said plunger and said body of said ampule include a plurality of opposing steps formed thereon, said plurality of steps on said plunger being operably connected to said plurality of steps on said body to form a tortuous path sterility barrier therebetween, and
        an orifice formed in said nozzle,
    a housing releasably attached to said ampule,
    a piercing cannula fixedly and axially located within said housing,
    a barrier axially and slidably located within said housing, said barrier being maintained in spaced relation with said cannula and said barrier being adapted to receive and retain a medication vial, and
    a push rod axially and slidably attached to said housing to drive medication from a medication vial retained by said barrier.

16. The ampule filling device of claim 15, wherein said ampule, housing, cannula and barrier assembly is bulk sterilized during manufacture.

17. An ampule filling device comprising
    an ampule, said ampule comprising
        a body having first and second ends, said first end opens into a storage cavity formed in said body and said second end is formed into a nozzle,
        a plunger axially and slidably extending from said first end into said storage cavity of said body, each of said plunger and said body of said ampule including a plurality of opposing steps formed thereon, said plurality of steps on said plunger being operably connected to said plurality of steps on said body to form a tortuous path sterility barrier therebetween, and
        an orifice formed in said nozzle,
    a housing releasably attached to said ampule,
    a piercing cannula fixedly and axially located within said housing,
    a barrier axially and slidably located within said housing,
    a medication vial having a piston axially and slidably located within said vial, said medication vial being axially received in said housing adjacent said barrier, and
    a push rod axially and slidably attached to said housing, said push rod including a rod axially extending into said housing and abutting said piston in said medication vial to drive medication from said medication vial during operation of the ampule filling device.

18. The ampule filling device of claim 17, wherein said ampule, housing, cannula and barrier assembly is bulk sterilized during manufacture.

19. An ampule filling device comprising
    a housing having a first and second chamber separated by a partition,
    a piercing cannula axially fixed in said partition, said cannula having a first end adjacent to said first chamber and a second end extending into said second chamber,
    an ampule releasably attached to said housing adjacent said first chamber,
    said ampule comprising
        a body having a first and second end, said first end opens into a storage cavity formed in said body and said second end is formed into a nozzle,
        a plunger axially and slidably extending from said first end into said storage cavity of said body, each of said plunger and said body of said ampule including a plurality of opposing steps formed thereon, said plurality of steps on said plunger being operably connected to said plurality of steps on said body to form a tortuous path sterility barrier therebetween, and
        an orifice formed in said nozzle,
    a barrier axially and slidably located within said second chamber, said barrier being maintained in spaced relation with said second end of said cannula prior to operation of the ampule filling device,
    a medication vial having a piston axially and slidably located within said vial, said medication vial being received and retained by said barrier, and
    a push rod axially and slidably attached to said housing, said push rod including a rod axially extending into said second chamber and abutting said piston in said medication vial to drive medication from said medication vial during operation of the ampule filling device.

20. An ampule filling device comprising
    an ampule,
    a housing releasably attached to said ampule, said housing comprising a transfer chamber, a supply chamber, and a partition interposing and separating said transfer and supply chambers, said transfer chamber further comprising a stem extending into said transfer chamber from said partition and forming a toroidal cavity with said housing and said partition,
    a piercing cannula fixedly and axially located in said partition and interconnecting said transfer chamber and said supply chamber,
    a barrier axially and slidably located within said housing adjacent an inner wall of said housing, said barrier being maintained in space relation with said cannula prior to operation of the ampule filling device, and said barrier including a cylindrical cavity adapted to receive and retain a sealed medicant filled vial, and
    a pushrod axially and slidably attached to said housing.

21. The ampule filling device of claim 20, wherein said stem includes a cavity comprising an inner wall inwardly tapered toward said partition and forming a female half of a slip taper fitting.

22. An ampule filling device comprising
    a housing having a first and second chamber separated by a partition, said first chamber further comprising a stem extending into said first chamber from said partition and forming a toroidal cavity with said housing and said partition, a piercing cannula axially fixed in said partition, said cannula having a first end adjacent to said first chamber and a second end extending into said second chamber, an ampule releasably attached to said housing adjacent said first chamber, a barrier axially and slidably located within said second chamber adjacent an inner wall of said housing, said barrier being maintained in spaced relation with said second end of said cannula prior to operation of the ampule filling device, a medication vial having a rubber closure on one end and a piston axially and slidably located within said vial, said medication vial being received and retained by said barrier, and a pushrod axially and slidably attached to said housing, said pushrod including a rod axially extending into said second chamber and abutting said piston in said medication vial to drive medication from said medication vial during operation of the ampule filling device.

23. The ampule filling device of claim 22, wherein said stem includes a cavity comprising an inner wall inwardly tapered toward said partition and forming a female half of a slip taper fitting.

* * * * *

UNITED STATES PATENT AND TRADEMARK OFFICE
CERTIFICATE OF CORRECTION

PATENT NO. : 5,649,912
DATED : July 22, 1997
INVENTOR(S) : Steven F. Peterson

It is certified that error appears in the above-indentified patent and that said Letters Patent is hereby corrected as shown below:

Column 2, line 45, change "untilled" to --unfilled--.

Column 3, line 66, change "untitled" to --unfilled--.

Signed and Sealed this

Twenty-third Day of December, 1997

Attest:

BRUCE LEHMAN

Attesting Officer

Commissioner of Patents and Trademarks